United States Patent [19]

Habdas et al.

[11] 4,251,342
[45] Feb. 17, 1981

[54] SOLID ELECTROLYTE OXYGEN SENSOR WITH INTEGRAL HEATER

[75] Inventors: Edward P. Habdas; Jon D. Aaron, both of Decatur, Ala.

[73] Assignee: UOP Inc., Des Plaines, Ill.

[21] Appl. No.: 57,624

[22] Filed: Jul. 16, 1979

[51] Int. Cl.³ ............................................. G01N 27/58
[52] U.S. Cl. ................................................. 204/195 S
[58] Field of Search .............................. 204/195 S, 1 S

[56] References Cited

U.S. PATENT DOCUMENTS

| 4,129,491 | 12/1978 | Obiaya | 204/195 S |
| 4,155,827 | 5/1979 | Maurer et al. | 204/195 S |
| 4,178,222 | 12/1979 | Murphy et al. | 204/195 S |

*Primary Examiner*—G. L. Kaplan

*Attorney, Agent, or Firm*—James R. Hoatson, Jr.; Barry L. Clark; William H. Page, II

[57] ABSTRACT

Solid electrolyte oxygen sensor incorporates a sealed integral heater which is positioned internally of the tubular wall of the ceramic sensor body in the region radially adjacent the disc shaped solid electrolyte which is mounted transverse to the axis of the body. A plurality of small longitudinal apertures are formed in the body wall by extrusion. A groove formed in the external side wall of the body provides access so that a resistance heating wire can be threaded alternately in opposite directions through the small apertures. The wire bends are accommodated by the side wall groove and an end wall groove, each of which can be sealed with a castable ceramic after the wire is installed.

8 Claims, 4 Drawing Figures

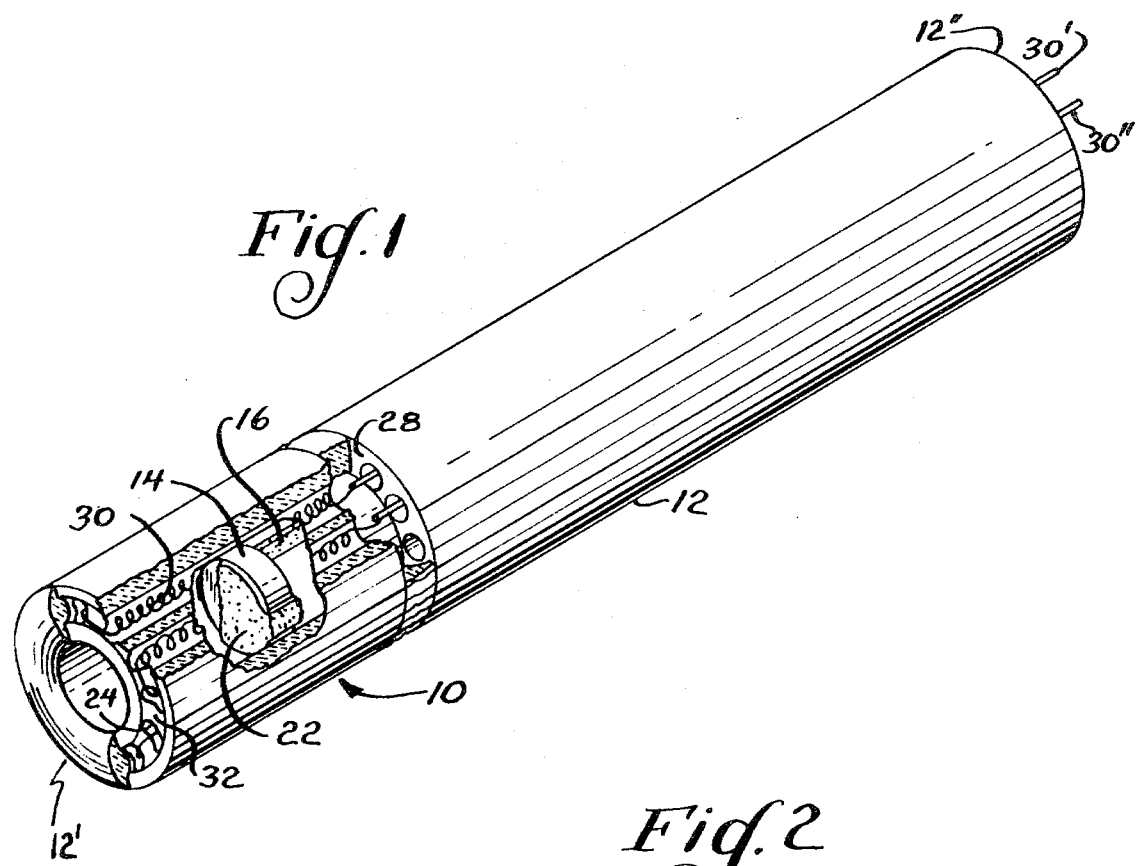
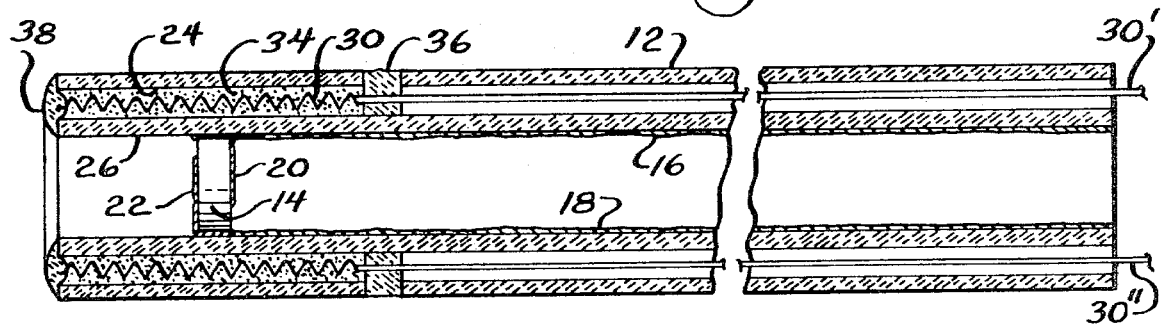
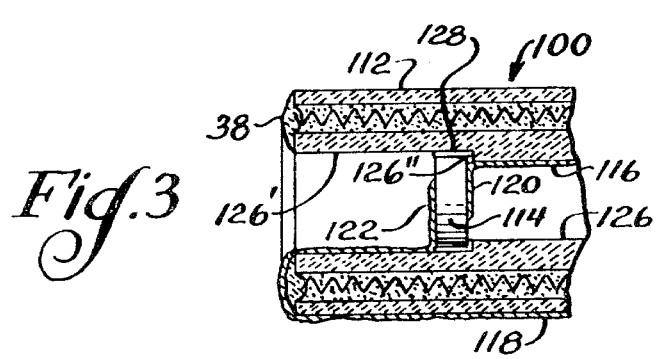
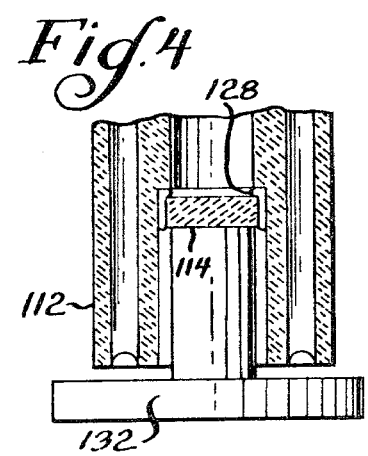

SOLID ELECTROLYTE OXYGEN SENSOR WITH INTEGRAL HEATER

BACKGROUND OF THE INVENTION

The invention relates to oxygen sensors and particularly to such sensors which utilize solid electrolytes which must generally operate at temperatures of at least about 800° F. In many situations, particularly the automotive field, the sensor's environment can maintain a sufficiently high temperature. Where it cannot, such as in many industrial applications, a separate heater must be provided. Even in some installations where there is sufficient heat, it is often desirable to maintain the sensor at some constant temperature somewhat above the maximum temperature of the process. With this latter arrangement the cell output is directly related to the familiar Nernst equation and can represent percent oxygen without the necessity of providing complex circuitry to account for variable temperatures.

Typically, oxygen sensors are constructed from ceramic materials in a tubular shape. An example of such a sensor for industrial use is Shum et al U.S. Pat. No. 4,119,513. Heaters, if provided, are generally constructed as separate items surrounding the sensor. This method interposes a thermal barrier between the heat source and sensor which can require heater temperatures considerably above the desired sensor temperature. These high temperatures require costly materials of construction for long life. If attempts are made to bond a separate heater to the sensor, then problems in materials arise. The heater material, adhesives, and sensor materials must be matched so as to prevent thermal stresses from arising, particularly during fast heat-up cycles. In addition many of the available high temperature adhesives require curing temperatures in excess of the allowable limits of the sensor and therefore are unusable. Some examples of gas sensor patents which include heating in one way or another are: U.S. Pat. Nos. 3,442,773; 3,597,345; 3,616,408; 3,871,981; 3,911,386; 3,915,828; 3,936,794 and 4,004,452.

SUMMARY

It is among the objects of the present invention to provide a solid electrolyte oxygen sensor which has an integral heater and which will be economical to manufacture, will require a minimal amount of energy input, will be long lasting, and will be undamaged by being operated at temperatures up to about 1500° F. for extended periods.

The sensor construction disclosed herein achieves the aforementioned advantages and others. The sensor includes a hollow ceramic body, preferably with an overall length of about 3-6" and an outside diameter after firing of about 0.5-0.75" with a disc or wafer of solid electrolyte sealed inside near one end. The ceramic is preferably of a type called forsterite which has a close thermal expansion match to yttria stabilized zirconium dioxide, a common solid electrolyte. In one embodiment, the forsterite body is extruded to about a 1" outer diameter with a central opening of about 0.375" diameter surrounded by a number of circumferentially located smaller holes of approximately 0.125" diameter which are adapted to contain heater elements. The number of holes can vary over a wide range, such as about 4-12, for example. Obviously, a larger number of holes will provide more uniform heating of the wafer or disc of solid electrolyte. When the forsterite is dried but still in the green state and easily machinable, it is cut to length and has a circumferential groove cut in its side to a width of about 0.125" and a depth about equal to that of the circumferential holes. A second groove is also cut in the end face of the sensing end on a diameter corresponding to the diameter of the circle containing the axes of the circumferential holes. The two grooves provide space for the return bends of the heater coils which are installed after the body is fired. The grooves are then filled with a castable ceramic to seal the heater coils. To improve heat transfer between the heater coils and the ceramic body a packing of grains of MgO or other suitable material is placed into the circumferential holes after the side groove is sealed. The solid electrolyte disc is preferably sealed and retained in the ceramic body by inherent shrinkage of the body during firing and a mechanical bonding that takes place as the surface of the forsterite body becomes glazed at the typical firing temperature of about 2370° F., as described in our co-pending application Ser. No. 55,573 filed July 9, 1979. Alternatively, the tube can be counterbored at its sensing end while in its green state to provide a shoulder or seat for supporting the electrolyte disc which may be sealed in place by a glass frit and electroded in the manner disclosed in the aforementioned U.S. Pat. No. 4,119,513.

BRIEF DESCRIPTION OF THE DRAWINGS

FIG. 1 is a partially broken away isometric view of the sensor of FIG. 2;

FIG. 2 is a side sectional view of the preferred embodiment of our improved oxygen sensor;

FIG. 3 is a fragmentary side sectional view illustrating a modified mounting for the sensor electrolyte; and FIG. 4 is a side sectional view illustrating the apparatus used to support the disc of FIG. 3 as it is sealed to the tube.

DESCRIPTION OF THE PREFERRED EMBODIMENTS

FIG. 1 shows a partially broken away isometric view of the improved sensor and heater assembly indicated generally at 10. The tubular portion 12 has a sensing end portion 12' and a reference end portion 12" which are separated by a solid electrolyte disc 14. A reference lead 16 and a sensing lead 18 are in intimate contact with a reference electrode 20 and a sensing electrode 22, respectively. The leads and electrodes are all preferably formed from the same material, preferably platinum paste, so as to eliminate secondary voltages which can be produced when dissimilar metals are used. A series of spaced small holes 24 are extruded the length of the tube 12 as the central aperture 26 is extruded. A circumferential groove 28 is machined in the side of the tube 12 to about the depth of the holes 24. This groove, which is about 0.125" wide, permits the heater wire 30 to be easily threaded back and forth between adjacent apertures 24 and accommodates the bends of the wire at the reference end of the heater while an end groove 32 accommodates the bends at the sensing end. The two ends 30', 30" of the wire 30 extend out of the reference end 12" of the sensor where they can be attached to a source of electrical power (not shown). The heater wire 30 is shown as extending a little more than the diameter of the disc 14 both axially forwardly and rearwardly of the disc 14 so as to insure uniform heating of the disc and its electrodes. A packing of MgO particles 34 in the heater wire containing holes 24 help conduct heat into the tube wall 12 and to the disc 14. A layer 36 of castable ceramic is used to close and seal the side groove 28 while a layer 38 of castable ceramic is used to close and seal the end wall groove 32. The layers 36, 38 also protect the heater wire 30 from damage by the ambient atmosphere, such as flue gases, to which the sensor 10 is normally subjected.

It will be noted that in FIGS. 1 and 2 the tube bore 26 is of constant diameter and the leads 16, 18 are each located on its inner wall with the disc 14 held by a shrink fit engagement caused by the shrinkage of the tube wall 12 during firing as explained in our co-pending application Ser. No. 55,573 which is incorporated by reference herein. Where the tube is made of forsterite, this shrinkage can be about 25% and produces an interference fit of about 5% which provides a quite effective mechanical seal which is highly resistant to thermal shock failure. Where this assembly method is used, the electrodes 20, 22 are applied to the pre-fired disc 14 and their edge portions are placed in alignment with the lead stripes 16, 18 on the tube inner surface so that a firm bond will be produced as the tube 12 shrinks about the disc 14 during firing of the tube to about 2370° F. Preferably, a platinum electrode paste is selected which has a melting point just 100°-200° F. below the tube firing temperature. After firing, the wire 30 is threaded into the holes 24 and the castable ceramic layers 36, 38 are added.

FIG. 3 shows a slightly modified sensor 100 which differs from the sensor 10 in that the disc 114 is attached after firing of the tube 112 rather than before. The inner tube wall 126 is counterbored in its green state to produce an enlarged diameter portion 126' and a recess 126'' which is slightly larger than the disc 114 after the tube is fired. The disc 114 is sealed to the tube wall 126' and recess 126'' by a layer 128 of glass frit such as Corning No. 1415 which is preferably mixed with alcohol as a binder and coated on the wall 126' and in the recess 126'' as well as around the edges of the disc 114. Heating to about 392° F. evaporates the solvent and causes the frit to form a caked powder fillet. The previously fired tube 114 is then refired at about 1850° F. with the disc on the fixture 132 shown in FIG. 4 and with the disc being located in a horizontal plane and the weight of the tube above it. This causes the glass frit to produce a better bond than where the heating takes place with the disc above the recess since any bubbles will be released and the glass will flow downwardly to fill the space between the disc and tube wall. After the glass frit has melted to produce a seal, the electrodes 120 and 122 and the leads 116 and 118, preferably platinum, are painted on in the manner disclosed in the aforementioned Shum et al U.S. Pat. No. 4,119,513. The leads and electrodes are then fired at a temperature of about 1750° F.

We claim as our invention:

1. An oxygen sensor comprising an elongated tubular ceramic body having a central aperture portion and a surrounding wall portion containing at least four spaced apertures, a disc of stabilized solid electrolyte mounted in said central aperture portion in the sensing end of said tubular body and transversely of the axis of said body so that a sensing side can be exposed to a gas to be sensed while a reference side is exposed to a reference gas, electrode means on the opposite sides of said disc and lead means electrically connected to said electrode means and extending to the reference end of said tubular body, electrical resistance heating means mounted in said at least four apertures in at least the region thereof which is close to, and radially outward of said disc, said heating means being sealed in said apertures in said region and having lead means extending to the reference end of said tubular body through at least two of said spaced apertures.

2. An oxygen sensor in accordance with claim 1 wherein said tubular ceramic body has a side groove around its periphery which extends to the depth of the spaced apertures, said side groove being positioned on the reference side of said disc of solid electrolyte, said electrical resistance heating means comprising a resistance wire which has a heating portion threaded fore and aft in alternate directions through said spaced apertures in the region between said side groove and an end face groove in the sensing end of said body, said wire also having end portions which comprise said lead means, said side and end grooves being filled with a cast ceramic to seal said heating portion in the region between said grooves.

3. An oxygen sensor in accordance with claim 2 wherein the apertures which carry the heating portion of said resistance wire are filled with grains of magnesium oxide.

4. An oxygen sensor in accordance with claim 2 wherein said heating portion extends in an axial direction along the length of said tubular body for a distance in both the sensing end and reference end directions which is at least as great as the diameter of the electrolyte disc.

5. An oxygen sensor in accordance with claim 1 wherein a pair of lead means are located internally of the reference end of said tubular body, said lead means being held in pressure electrical contact with edge located portions of the electrode means for each side of said disc by an interference fit between said body and disc.

6. An oxygen sensor in accordance with claim 1 wherein said disc is sealed by a melted glass frit to the sides and bottom surface of a recess formed in the sensing end of said tubular body.

7. An oxygen sensor in accordance with claim 6 wherein a platinum electrode is applied to each of the sensing and reference surfaces of said disc and a platinum sensing lead in contact with the sensing electrode passes along the inner wall of the sensing end of said tube, over the end wall and along the outer surface of the tube to the reference end thereof, a platinum reference lead in contact with the reference electrode passing internally of the tube to the reference end thereof.

8. An oxygen sensor in accordance with claim 7 wherein the disc is sealed by a melted glass frit to the sides and bottom surface of a recess formed in the sensing end of said tubular body.

* * * * *